United States Patent [19]

Chatterjee et al.

[11] Patent Number: 4,866,172
[45] Date of Patent: Sep. 12, 1989

[54] PRISTINAMYCIN PROCESS

[75] Inventors: Devnandan Chatterjee; Neil V. Harris; Trevor Parker; Christopher Smith; Peter J. Warren, all of Dagenham, England

[73] Assignee: May & Baker Limited, Dagenham, England

[21] Appl. No.: 183,310

[22] Filed: Apr. 12, 1988

Related U.S. Application Data

[63] Continuation of Ser. No. 70,378, Jul. 7, 1987, abandoned.

[30] Foreign Application Priority Data

Jul. 9, 1986 [GB] United Kingdom ............... 8616768

[51] Int. Cl.$^4$ .................... C07D 498/14; C07K 5/12; A61K 31/42
[52] U.S. Cl. .................. 540/456; 540/455; 530/317
[58] Field of Search .................. 540/456, 455

[56] References Cited

U.S. PATENT DOCUMENTS 4,668,669  5/1987  Barriere et al. ................... 540/455

FOREIGN PATENT DOCUMENTS 0133098  2/1985  European Pat. Off. ........... 540/455
0191662  8/1986  European Pat. Off. .

OTHER PUBLICATIONS

Chemical Abstracts, vol. 62 (1965), abstracting Preud'homme et al. in "Comptus. Rend.", vol. 260, No. 4, pp. 1309-1312 (1965) (French).
Chemical Abstracts, vol. 69, (1968), Item 10707z, abstracting Preud'homme et al., in "Bull. Soc. Chim Fr", (1968)(No. 2), pp. 585-591 (French).
Chemical Abstracts, vol. 71, (1969), Item 47912e, abstracting Delepipe in "G-I-T (Glas-Instrum-Tech.)", Fachz. Lab. (1964), vol. 13, No. 2, pp. 99-100 (German).
Djerassi et al., "J. Am. Chem. Soc." (1953), vol. 75, pp. 3833-3840.
Berkowitz et al., "J. Am. Chem. Soc.", (1958), vol. 80, pp. 6682-6684.
Bettoni et al., "J. Org. Chem.", (1976), vol. 41, pp. 2780-2781.
Sheehan et al., "J. Org. Chem.", (1974), vol. 39, pp. 2264-2266.
Yoshifugi et al., "Chem. Pharm. Bull.", (1985), vol. 26, pp. 5515-5521.
Mori et al., "Tetrahedron Letters", vol. 26, No. 48, pp. 5947-5950 (1985).
Colonna, "J.C.S. Chem. Comm.", (1975), pp. 71-72.
Carlsen et al., "J. Org. Chem.", (1981) vol. 46, pp. 3936-3938.
Tanaka et al., "Chem. Pharm. Bull.", (1987), vol. 35, pp. 364-369.
Paris et al., "Pathology and Biology", (1985), pp. 493-496.
Nagao et al., 26th Symposium on the Chemistry of Natural Products, Kyoto (1983), Symposium Papers, pp. 476-484.
Fatiadi, Synthesis, 1974, pp. 229-272, especially pp. 255-257.
Chemical Abstracts, vol. 100, 1984, p. 564, No. 209476n.
Chemical Abstracts, vol. 105, 1985, p. 413, abstract No. 119846r.
Bull. Soc. Shimique De France, No. 2, 1968, pp. 585-591.

Primary Examiner—Robert T. Bond
Attorney, Agent, or Firm—Stevens, Davis, Miller & Mosher

[57] ABSTRACT

There is described a process for the preparation of therapeutically useful pristinamycin II$_B$ sulphone derivatives.

Also disclosed are compounds of general formula (I) in which n is equal to 2 in the form of their B isomers, and certain novel compounds of general formula (I) in which n is equal to 2.

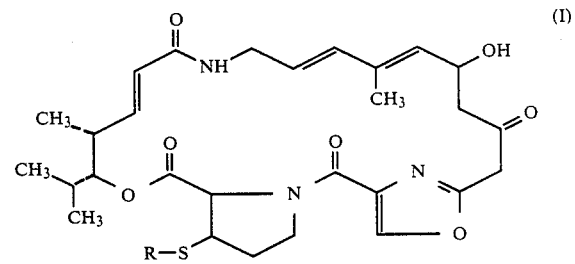

(I)

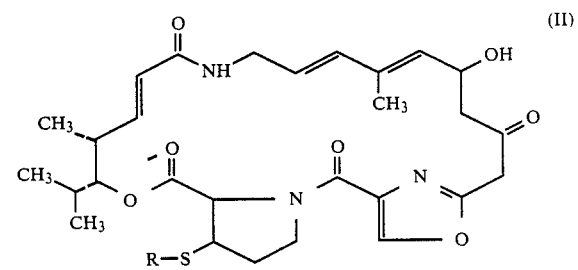

(II)

8 Claims, No Drawings

PRISTINAMYCIN PROCESS

This application is a continuation of application Ser. No. 070,378 filed July 7, 1987.

The present invention relates to the preparation of therapeutically useful pristinamycin II$_B$ sulphone derivatives.

European Patent Publication No. 191662 describes inter alia therapeutically useful pristinamycin II$_B$ derivatives, of the general formula (I) hereinafter depicted, and their acid addition salts, in which R denotes: either a nitrogen-containing 4 to 7-membered heterocyclic ring radical, which may contain 1 or more other hetero atoms chosen from nitrogen, oxygen and sulphur in the form of sulphoxide or sulphone, and unsubstituted or substituted by alkyl; or alkyl of 2 to 4 carbon atoms substituted by 1 or 2 radicals chosen from phenyl, cycloalkylamino of 3 to 6 ring atoms, N-alkyl-N-cycloalkylamino of 3 to 6 ring atoms, alkylamino, dialkylamino and dialkylcarbamoyloxy, the alkyl parts of these 2 latter radicals being unjoined or joined to form, with the nitrogen atom to which they are attached, a saturated or unsaturated 4 to 7-membered heterocyclic ring which may contain another hetero atom chosen from nitrogen, oxygen and sulphur in the form of sulphoxide or sulphone, and unsubstituted or substituted by alkyl, or alkyl of 2 to 4 carbon atoms substituted by one or more nitrogen-containing, 4 to 7-membered hetercyclic rings which may contain 1 or 2 other hetero atoms chosen from nitrogen, oxygen and sulphur in the form of sulphoxide or sulphone, and unsubstituted or substituted by alkyl, these heterocyclic rings being linked to the alkyl by a carbon atom of the ring, at least one of the substituents carried by the said alkyl chain being a nitrogen-containing substituent capable of forming salts, or the [(S)-1-methyl-2-pyrrolidinyl] methyl group, and n is 1 or 2. The alkyl radicals and moieties referred to above are linear or branched and, unless mentioned otherwise, contain 1 to 10 carbon atoms.

The compounds of formula (I) have isomeric forms and their isomers and their mixtures are included within the terms of the description herein.

When R denotes a heterocyclic radical, this radical can be, for example: 3-azetidinyl, 3-pyrrolidinyl, 3- or 4-piperidyl or 3- or 4-azepinyl.

When R denotes an alkyl radical substituted by a heterocyclic ring radical, the heterocyclic ring radical can be chosen, for example, from the radicals listed above or the 2-azetidinyl, 2-pyrrolidinyl, 2-piperidyl, 2-azepinyl, piperazinyl, 4-alkylpiperazinyl, quinolyl, isoquinolyl or imidazolyl radicals.

When R contains a dialkylamino or dialkylcarbamoyloxy radical in which the alkyl moieties form a heterocyclic ring with the nitrogen atom to which they are attached, this ring can be chosen, for example, from: 1-azetidinyl, 1-pyrrolidinyl, piperidino, 1-azepinyl, morpholino, thiomorpholino in the form of sulphoxide or sulphone, 1-piperazinyl, 4-alkyl-1-piperazinyl, N-alkyl-1- homopiperazinyl, or 1-imidazolyl.

According to European Patent Publication No. 191662 the compounds of general formula (I) may be prepared by oxidation of a derivative of pristinamycin II$_B$, of its salt or of a protected derivative, of general formula (II) in which R is defined as above, it being understood that in the cases where R contains a sulphur-containing heterocyclic ring, the sulphur atom can be in the form of a sulphide, sulphoxide or sulphone.

Among the oxidizing agents which are stated to be suitable for preparing a compound of general formula (I) in which n=1, are organic peracids: percarboxylic or persulphonic acids (for example peracetic, pertrifluoroacetic, performic, perbenzoic, m-chloroperbenzoic, p-nitroperbenzoic, permaleic, monoperphthalic, percamphoric or p-toluenepersulphonic acids) and inorganic peracids (for example periodic or persulphuric acid).

When the intention is to prepare a compound of general formula (I) in which n=2, the oxidation may be carried out with selenium dioxide and hydrogen peroxide, using a salt of the compound of general formula (II), or with a peracid such as those referred to above, especially pertrifluoroacetic acid, or m-chloroperbenzoic acid.

The compounds of general formula (II) can be prepared by the reaction of a compound of general formula:

R—SH    (III)

in which R is defined as above, with the compound of formula (IV) that is to say pristinamycin II$_A$.

The reaction is usually carried out in an organic solvent such as an alcohol such as methanol or ethanol, or a chlorinated solvent such as methylene chloride, 1,2-dichloroethane or chloroform, or in a mixture of these solvents (for example methylene chloride/methanol) at a temperature between -30° and 50° C.

Occasionally it may be advantageous to operate in the presence of a tertiary amine, for example triethylamine, or of an ethanolamine (for example dimethylethanolamine).

When R denotes a radical containing a secondary amine group capable of interfering with the reaction, this group should be protected beforehand, before the compound of general formula (III) is reacted with the compound of formula (IV). Any usual means which enables a secondary amine function to be blocked in the form of a labile radical can be used for this purpose. It is especially advantageous to use the trifluoroacetyl radical as a blocking radical which can be removed as described above. In such a case, however, it is not absolutely essential to remove the protective radical, and the protected derivative can be used directly in the oxidation reaction.

The compounds of general formula (I) in which n is equal to 2 can also be prepared by the oxidation of a compound of general formula (I) in which n is equal to 1.

The reaction may be carried out under conditions which are similar to the conditions described above for preparing a compound of general formula (I) in which n =2 starting from a pristinamycin II$_B$ derivative of general formula (II).

It has now been found that the compounds of formula (I) in which n is 2 may be made by the oxidation of the compounds of general formula (I) in which n is equal to 1 and of the compounds of general formula (II) with a combination of a periodate and a ruthenium (VIII) compound.

Accordingly, the present invention provides a process for the preparation of the compounds of formula (I) in which n is equal to 2 which comprises oxidising a compound of general formula (I) in which n is equal to 1 or a compound of general formula (II) with a periodic acid salt and a catalytic amount of ruthenium (VIII), which may optionally be prepared in situ by oxidation of a ruthenium compound of a lower oxidation state.

The reaction may be carried out in an aqueous medium, e.g. acetone-water or acetonitrile-water, acetonitrile-dilute aqueous hydrogen chloride solution, ethanol-water, dimethylformamide-water or dilute aqueous hydrogen chloride solution, or an inert organic solvent substantially immiscible with water, for example a chlorinated hydrocarbon e.g. dichloromethane, at a temperature from $-5°$ C. to ambient temperature (e.g. 25° C.).

The ruthenium (VIII) catalyst may be derived from for example ruthenium tetroxide, ruthenium dioxide dihydrate or tris(triphenylphosphine)-ruthenium (II) chloride, or preferably ruthenium trichloride trihydrate.

A preferred process according to the present invention comprises the oxidation of a compound of general formula (II) using a periodic acid salt and a catalytic amount of ruthenium trichloride trihydrate in acetonitrile and water.

A preferred process according to the present invention comprises the oxidation of a compound of general formula (I) in which n is equal to 1 using a periodic acid salt and a catalytic amount of ruthenium trichloride trihydrate in dichloromethane and water.

The periodic acid salt, which may be an alkali metal periodate e.g. sodium or potassium metaperiodate, is preferably used in a large equivalent excess in aqueous solution or as solid. The preferred ratio is 1.6:1 to 5:1 (for example 2.8:1 to 5:1) mol, preferably 1.6:1 to 3:1 mol, when the starting material is a compound of general formula (I) in which n is equal to 1, or 5:1 to 7:1 mol, preferably 5:1 or 6:1 mol, when the starting material is a compound of general formula (II).

A preferred process according to the present invention comprises the oxidation of a compound of general formula (1) in which n is equal to 1 using a periodic acid salt and a catalytic amount of ruthenium trichloride trihydrate in which the molar ratio of periodic acid salt: compound of general formula (I) in which n is equal to 1 is 1.6:1 mol in dichloromethane and water.

When the starting material is a compound of general formula (II) the process according to the invention also gives some compound of general formula (I) in which n is equal to 1.

The process of the present invention gives a better yield and cleaner product than that exemplified in European Patent Publication No. 191662.

According to a further feature of the present invention, there are provided compounds of general formula (I) in which n is equal to 2 in the form of their isomers B as hereinafter defined and pharmaceutically acceptable acid addition salts thereof. 26-(2-diethylaminoethyl)sulphonylpristinamycin II$_B$ (isomer B is similar in its biological activity to the corresponding isomer A described in European Patent Publication No. 191662.

The process of the present invention is especially useful for the preparation of the following:
26-(2-diethylaminoethyl)sulphonylpristinamycin II$_B$
26-(2-diisopropylaminoethyl)sulphonylpristinamycin II$_B$; and the following novel compounds
26-(2-dipropylaminoethyl)sulphonylpristinamycin II$_B$
26-(2-dibutylaminoethyl)sulphonylpristinamycin II$_B$
26-(N-ethyl-N-isopropyl-2-aminoethyl)sulphonylpristinamycin II$_B$
26-[2-(1-pyrrolidinyl)ethyl]sulphonylpristinamycin II$_B$
26-(2-morpholinoethyl)sulphonylpristinamycin II$_B$
26-(2-dimethylaminoethyl)sulphonylpristinamycin II$_B$
26-(N-butyl-N-methyl-2-aminoethyl)sulphonylpristinamycin II$_B$ and 26-(2-piperidinoethyl)sulphonylpristinamycin II$_B$ in the form of their isomers A or B and pharmaceutically acceptable acid addition salts thereof.

The compounds of general formula (I) can be purified by known methods, for example by crystallization, chromatography or successive extractions in an acidic or basic medium.

The following examples show how the invention can be put into practice. The NMR spectra of the compounds illustrated in these examples show general characteristics which are common to all the compounds of general formula (I) and individual characteristics which are specific to each of the compounds, depending on the substituents. Only the individual characteristics due to the changeable radicals are mentioned in the examples which follow. For the compounds of general formula (I), all the protons are designated according to the numbering indicated in the following formula (V).

Unless stated otherwise, all the spectra were recorded at 250 MHz in deuterochloroform; the chemical shifts are expressed in ppm relative to the tetramethylsilane signal. The abbreviations used in the following text are as follows:
s=singlet
d=doublet
t=triplet
mt=multiplet
m=unresolved bands
dd=doublet of doublets
dt=doublet of triplets
ddd=doublet of doublets of doublets
dddd=doublet of doublets of doublets of doublets It is to be understood that the various isomers have been classified arbitrarily according to the chemical shifts observed in NMR.

The names isomer $A_1$ and isomer $A_2$ of the compounds of general formula (I) in which n=1 are given to the isomers which have the characteristics: approximately 1.7 (s, —CH$_3$ at 33); approximately 3.8 (s, >CH$_2$ at 17); <5 (d, —H$_{27}$)isomer A$_2$ or >5 (d, —H$_{27}$) isomer A$_1$; approximately 5.50 (broad d, —H$_{13}$); approximately 6.20 (d, —H$_{11}$); approximately 6.6 (>NH at 8); ≧8 (s, —H$_{20}$).

The names isomer B$_1$ and isomer B$_2$ of the compounds of general formula (I) in which n=1 are given to the isomers which have the characteristics: approximately 1.5 (s, —CH$_3$ at 33); approximately 3.7 and 3.9 (2d, >CH$_2$ at 17); approximately 4.8 (mt, —H$_{13}$) ; <5 (d, —H$_{27}$) isomer B$_2$ or >5 (d, —H$_{27}$) isomer B$_1$; approximately 5.70 (borderline AB, —H$_{11}$ and —H$_{10}$); approximately 7.7 (>NH at 8); approximately 7.8 (s, —H$_{20}$).

The name isomer A of the compound of general formula (II) is given to the isomer which has NMR characteristics identical to those listed above for the isomers A$_1$ and A$_2$ of the compounds of general formula (I), it being understood that the H at 27 is characterized by: 4.7 (d, J≦1 Hz).

The name isomer B of the compound of general formula (II) is given to the isomer which has NMR characteristics identical to those listed above for the isomers B$_1$ and B$_2$ of the compounds of general formula (I), it being understood that the H at 27 is characterized by: 4.6 (d, J≧2.5 Hz).

In the following examples, the name "flash" chromatography is given to a purification technique in which a short chromatography column is used and operated under an intermediate pressure (50 kPa) with the use of a silica with a particular size distribution of 40–53 μm, according to W. C. Still, M. Kahn and A. Mitra (J.Org.-Chem. 43, 2923 (1978).

In the examples described below, unless stated otherwise, all the compounds can be dissolved at a strength of at least 2%, in the form of a hydrochloride.

EXAMPLE 1

To a stirred solution of 26-(2-diisopropylaminoethyl)-sulphinylpristinamycin II$_B$ (isomer A$_2$) (10 g) in dichloromethane (300 cc) was added a solution of sodium metaperiodate (8.5 g) in distilled water (75 cc). The pH of the aqueous phase was adjusted from 6 to 7 by addition of solid sodium bicarbonate portionwise with rapid stirring of the mixture. The stirred two-phase system was cooled to 10° C. and ruthenium dioxide dihydrate (10 mg) was added. After stirring at 10° C. for 4 hours the reaction mixture was allowed to reach room temperature and the organic phase separated. The aqueous phase was adjusted to pH 7.5 by addition of solid sodium bicarbonate then extracted twice with dichloromethane (70 cc). The combined organic phases were dried over anhydrous sodium sulphate, evaporated to dryness under reduced pressure at 40°–45° C. and the residual yellow-brown solid (10 g) was dissolved in ethyl acetate (300 cc). The solution was washed repeatedly with pH 4 citrate buffer solution (10×60 cc) until there was little product remaining in the ethyl acetate solution (monitored by thin layer chromatography and h.p.l.c.). The citrate buffer washings were adjusted to pH 7.5 by addition of solid sodium bicarbonate portionwise with stirring and the solution extracted with dichloromethane (100 cc then four lots of 50 cc). The combined extracts were dried over anhydrous sodium sulphate and evaporated under reduced pressure at 40°–45° C. affording a yellow solid (6.8 g) which was purified by "flash" chromatography [eluent: ethyl acetate-methanol (92-8 by volume)] 30 cc fractions being collected. Fractions 14-30 were combined and concentrated to dryness under reduced pressure at 40°–45° C. affording a white solid (3.99 g). Further purification of 2.56 g of this material was carried out by "flash" chromatography [eluent:chloroform-methanol (95-5 by volume)] 14 cc fractions being collected. Fractions 32-50 were combined and concentrated to dryness to give a white solid (2.24 g) which was dissolved in ethyl acetate (10 cc). The solution was slowly added to light petroleum (b.p. 40°-60° C.) (100 cc) and the precipitate separated off by filtration to give 26-(2-diisopropylaminoethyl)sulphonylpristinamycin II$_B$ (isomer A) as a white powder (2.1 g) melting slowly with decomposition above 110° C. Found: C, 60.3; H, 7.5; N, 7.6%. Calculated for C$_{36}$H$_{54}$N$_4$O$_9$S: C, 60.1; H, 7.57; N, 7.79%.

NMR data confirmed this is identical to the compound of Example 25 of European Patent Publication No. 191662.

EXAMPLE 2

To a vigorously stirred mixture of pH 8 buffer solution (350 cc) and dichloromethane (350 cc) was added in one portion sodium metaperiodate (9.1 g), at ambient temperature, immediately followed by 26-(2-diethylaminoethyl)sulphinylpristinamycin II$_B$ (isomer A$_2$) (8.5 g). After 1 minute ruthenium dioxide dihydrate (50 mg) was added, also in one portion. After stirring vigorously for 10 minutes the mixture was decanted into a separating funnel, the reaction flask being washed with fresh dichloromethane (175 cc). The layers were separated and the organic phase was washed with water (200 cc), dried over anhydrous magnesium sulphate and evaporated to give a light brown powder (5.6 g). This powder was shaken with a mixture of ethyl acetate (150 cm$^3$) and pH 4 buffer solution (100 cm$^3$). After decantation from a small amount of insoluble tar the layers were separated and the organic phase was re-extracted with pH 4 buffer solution (2×50 cc). The combined buffer solutions were backwashed with ethyl acetate (3×25 cc), saturated with solid sodium hydrogen carbonate and extracted with dichloromethane (100 cc, then 2×50 cc). The combined organic extracts were dried over anhydrous magnesium sulphate and evaporated to give a light yellow powder (4.3 g). This was dissolved in ethyl acetate (40 cc), filtered to remove insoluble material and evaporated to give 26-(2-diethylaminoethyl)sulphonylpristinamycin II$_B$ (isomer A) as a light yellow powder (3.7 g) melting slowly with decomposition above 105° C. Found: C, 59.1; H, 7.5; N, 7.9; S, 4.6%. Calculated for C$_{34}$H$_{50}$N$_4$O$_9$S:C, 59.1; H, 7.3; N, 8.11; S, 4.6%.

NMR data confirmed this is identical to the compound of Example 24 of European Patent Publication No. 191662.

EXAMPLE 3

A solution of sodium metaperiodate (16.2 g) in water (500 cc) was added as rapidly as possible in one portion to a vigorously stirred solution of 26-(2-diethylaminoethyl)thiopristinamycin II$_B$ (isomer A) (10.0 g) in acetone (500 cc) at room temperature, followed 15 seconds later, by the addition of ruthenium dioxide hydrate (50 mg), also in one portion. After stirring at room temperature for 10 minutes, during which time a white precipitate had formed, solid sodium hydrogen carbonate (20 g) was added. After stirring for a further 1 minute the mixture was filtered through diatomaceous earth, the filter pad being washed with dichloromethane (750 cc). The filtrate was mixed thoroughly, the layers allowed to separate and the aqueous layer was re-extracted with fresh dichloromethane (250 cc); the addition of solid sodium chloride at this point aided the separation of the two layers. The combined dichloromethane extracts were dried over anhydrous magnesium sulphate and evaporated to give 7.8 g of a light brown powder. This product was shaken well with ethyl acetate (150 cc) for 5 minutes, filtered to remove insoluble material and the filter pad washed with fresh ethyl acetate (50 cc). Evaporation of the combined filtrates gave 26-(2-diethylaminoethyl)sulphonylpristinamycin II$_B$ (isomer A) as a light yellow powder (6.1 g).

By proceeding in a similar manner but replacing the 26-(2-diethylaminoethyl)thiopristinamycin II$_B$ (isomer A) by 26-(2-diisopropylaminoethyl)thiopristinamycin II$_B$ (isomer A), there was prepared 26-(2-diisopropylaminoethyl)sulphonylpristinamycin II$_B$ (isomer A).

By proceeding in a similar manner, but replacing the 26-(2-diethylaminoethyl)thiopristinamycin II$_B$ (isomer A) by 26-(2-diethylaminoethyl)thiopristinamycin II$_B$ (isomer B) and carrying out the reaction at 12° C., there was prepared 26-(2-diethylaminoethyl)sulphonylpristinamycin $II_B$ (isomer B) as a yellow amorphous powder. Purification of this material was carried out by "flash" chromatography [eluent: chloroform-methanol (95-5 by volume)] 30 cc fractions being collected. Fractions 21-23 were combined and concentrated to dryness under reduced pressure to give 26-(2-diethylaminoethyl)sulphonylpristinamycin $II_B$ (isomer B) as a white powder melting slowly from 98° C. Found: C, 56.2; H, 7.0; N, 7.3; S, 4.55%. Calculated for $C_{34}H_{50}N_4O_9S.2H_2O$: C, 56.2; H, 7.49; N, 7.71, S, 4.41%.

By proceeding in a similar manner, but replacing the 26-(2-diethylaminoethyl)thiopristinamycin $II_B$ (isomer A) by 26-(2-diethylaminoethyl)sulphinylpristinamycin $II_B$ (isomer $A_2$) and using 2.8 equivalents of sodium metaperiodate, there was prepared 26-(2-diethylaminoethyl)sulphonylpristinamycin $II_B$ (isomer A).

By proceeding in a similar manner, but replacing the 26-(2-diethylaminoethyl)thiopristinamycin $II_B$ (isomer A) with 26-(2-diethylaminoethyl)sulphinylpristinamycin $II_B$ (isomers $A_1+A_2$) and using 2.8 equivalents of sodium metaperiodate, there was prepared 26-(2-diethylaminoethyl)sulphonylpristinamycin $II_B$ (isomer A).

By proceeding in a similar manner, but replacing the 26-(2-diethylaminoethyl)thiopristinamycin $II_B$ (isomer A) with 26-(2-diisopropylaminoethyl)sulphinylpristinamycin $II_B$ (isomers $A_1+A_2$) and using 2.8 equivalents of sodium metaperiodate, there was prepared 26-(2-diisopropylaminoethyl)sulphonylpristinamycin $II_B$ (isomer A).

By proceeding in a similar manner, but replacing the 26-(2-diethylaminoethyl)thiopristinamycin $II_B$ (isomer A) by 26-(N-ethyl-N-isopropyl-2-aminoethyl)thiopristinamycin $II_B$ (isomer A), precooling the solution of sodium metaperiodate in water to 12° C., and carrying out the reaction at 6° C., there was prepared 26-(N-ethyl-N-isopropyl-2-aminoethyl)sulphonylpristinamycin $II_B$ (isomer A) as a pale yellow powder. Purification of this material was carried out by "flash" chromatography [eluent:chloroform-methanol (95 to 5 by volume)] 25 cc fractions being collected. Fractions 10-13 were combined and concentrated to dryness, the residue being dissolved in ethyl acetate followed by evaporation to remove residual traces of chloroform, affording 26-(N-ethyl-N-isopropyl-2-aminoethyl)sulphonylpristinamycin $II_B$ (isomer A) as a pale yellow powder melting slowly 103° to 110° C. Found : C, 58.7; H, 7.4; N, 7.6; S, 4.4%. Calculated for $C_{35}H_{52}N_4O_9S$ . 0.5 $CH_3CO_2CH_2CH_3$: C, 59.3; H, 7.54; N, 7.48; S, 4.28%.

By proceeding in a similar manner, but replacing the 26-(2-diethylaminoethyl)thiopristinamycin $II_B$ (isomer A) by 26-[2-(1-pyrrolidinyl)ethyl]thiopristinamycin $II_B$ (isomer A), precooling the solution of sodium metaperiodate in water to 12° C., and carrying out the reaction at 6° C., there was prepared 26-[2-(1-pyrrolidinyl)ethyl]sulphonylpristinamycin $II_B$ (isomer A) as a pale yellow powder. Purification of this material was carried out by "flash" chromatography [eluent:chloroform-methanol (95 to 5 by volume)] 25 cc fractions being collected. Fractions 23-32 were combined and concentrated to dryness, the residue being dissolved in ethyl acetate followed by evaporation to remove residual traces of chloroform, affording 26-[2-(1-pyrrolidinyl)ethyl]sulphonylpristinamycin $II_B$ (isomer A) as a pale yellow powder, melting slowly 110° to 117° C. Found: C, 59.6; H, 7.2; N, 7.7; S, 4.6%. Calculated for $C_{34}H_{48}N_4O_9S$ . 0.5 $CH_3CO_2CH_2CH_3$: C, 59.0; H, 7.15; N, 7.65; S, 4.38%.

By proceeding in a similar manner, but replacing the 26-(2-diethylaminoethyl)thiopristinamycin $II_B$ (isomer A) by 26-(2-morpholinoethyl)thiopristinamycin $II_B$ (isomer A), precooling the solution of sodium metaperiodate in water to 12° C., and carrying out the reaction at 6° C., there was prepared 26-(2-morpholinoethyl)sulphonylpristinamycin $II_B$ (isomer A) as a pale yellow powder. Purification of this material was carried out by "flash" chromatography [eluent:chloroform-methanol (95 to 5 by volume)] 25 cc fractions being collected. Fractions 17-21 were combined and concentrated to dryness, the residue being dissolved in ethyl acetate followed by evaporation to remove residual traces of chloroform, affording 26-(2-morpholinoethyl)sulphonylpristinamycin $II_B$ (isomer A) as a white powder melting slowly above 108° C. Found : C, 57.7; H, 7.0; N, 7.6; S, 4.2%. Calculated for $C_{34}H_{48}N_4O_{10}S$ . 0.5 $CH_3CO_2CH_2CH_3$: C, 57.7; H, 7.0; N, 7.48; S, 4.28%.

EXAMPLE 4

A solution of sodium metaperiodate (7.3 g) in water (90 cc) was added as rapidly as possible in one portion to a vigorously stirred solution of 26-(2-dimethylaminoethyl)thiopristinamycin $II_B$ (isomer A)(4.66 g) in acetone (90 cc) at 15° C. followed, one minute later, by the addition of ruthenium dioxide dihydrate (50 mg), also in one portion. After stirring at room temperature for 15 minutes, during which time a white precipitate had formed, solid sodium bicarbonate (4.6 g) was added. After stirring for a further one minute the mixture was filtered, the filter pad being washed with dichloromethane (300 cc). The filtrate was mixed thoroughly, the layers allowed to separate and the aqueous layer was re-extracted with fresh dichloromethane (2×100 cc). The combined dichloromethane extracts were dried over anhydrous magnesium sulphate and evaporated to give 3.6 g of a light brown powder which was purified by "flash" chromatography [eluent:chloroform-methanol (95 to 5 by volume)] 20 cc fractions being collected. Fractions 23-45 were combined and concentrated to dryness under reduced pressure to give a white solid (1.3 g) which was dissolved in ethyl acetate (10 cc). The solution was slowly added to light petroleum (b.p. 40°-60° C.)(300 cc) and the precipitate separated off by filtration affording 26-(2-dimethylaminoethyl)sulphonylpristinamycin $II_B$ (isomer A) monohydrate as a white powder (0.7 g), m.p. 120°-122° C. Found : C, 56.9; H, 6.96; N, 8.0; S, 4.61%. Calculated for $C_{32}H_{46}N_4O_9S.H_2O$: C, 56.5; H, 7.10; N, 8.23; S, 4.70%.

By proceeding in a similar manner to that hereinbefore described but replacing the 26-(2-dimethylaminoethyl)thiopristinamycin $II_B$ (isomer A) by 26-(N-butyl-N-methyl-2-aminoethyl)thiopristinamycin $II_B$ (isomer A) there was prepared 26-(N-butyl-N-methyl-2-aminoethyl)sulphonylpristinamycin $II_B$ (isomer A) monohydrate as a cream coloured solid m.p. 118°-121° C. Found : C, 58.7; H, 7.20; N, 7.70; S, 4.50%. Calculated for $C_{35}H_{52}N_4O_9S.H_2O$: C, 58.2; H, 7.53; N, 7.75; S, 4.43%.

By proceeding in a similar manner to that hereinbefore described but replacing the 26-(2-dimethylaminoethyl)thiopristinamycin $II_B$ (isomer A) by 26-(2-piperidinoethyl)thiopristinamycin $II_B$ (isomer A) there was prepared 26-(2-piperidinoethyl)sulphonylpristinamycin $II_B$ (isomer A) monohydrate as a white powder. Found: C, 59.2; H, 7.20; N, 7.80, S, 4.6%. Calculated for $C_{35}H_{50}N_4O_9S.0.5H_2O$: C, 59.0; H, 7.15; N, 7.86; S, 4.5%.

By proceeding in a similar manner to that hereinbefore described but replacing the 26-(2-dimethylaminoethyl)thiopristinamycin II$_B$ (isomer A) by 26-(2-di-n-butylaminoethyl)thiopristinamycin II$_B$ (isomer A) there was prepared 26-(2-di-n-butylaminoethyl)sulphonylpristinamycin II$_B$ (isomer A) as a light yellow powder, melting slowly above 90° C. Found: C, 60.9; H, 7.9; N, 7.0; S, 4.2%. Calculated for $C_{38}H_{58}N_4O_9S$: C, 61.1; H, 7.8; N, 7.5%; S, 4.3%.

EXAMPLE 5

A solution of 26-(2-di-n-propylaminoethyl)thiopristinamycin II$_B$ (isomer A) (20.6 g) in acetone (1030 cc) and water (1030 cc) was cooled to 0° C. (internal temperature) with stirring. Ruthenium dioxide dihydrate (0.103 g) was added followed by sodium metaperiodate (38.72 g). After stirring at 0° C. to −5° C. for 1 hour solid sodium bicarbonate (20.6 g) was added, the mixture filtered and the residue washed with dichloromethane (1000 cc). The filtrate and washings were thoroughly mixed, the organic phase separated and the aqueous phase further extracted with dichloromethane (3×200 cc). The combined organic phases were dried over anhydrous magnesium sulphate and evaporated under reduced pressure at 40°–45° C. affording a cream coloured solid (16.9 g). 11.2 g of this material was heated with ethyl acetate (175 cc) and the mixture filtered to remove insoluble material (1.2 g) then cooled to 0° C. to 5° C. overnight and again filtered. The filtrate was concentrated to 70 cc volume and the solution slowly added to light petroleum (b.p. 40°–60° C.) (700 cc). The resulting precipitate was separated off by filtration to give 26-(2-di-n-propylaminoethyl)sulphonylpristinamycin II$_B$ hydrate (isomer A) as a cream coloured solid (7.8 g) melting point 129°–131° C. with decomposition. Found: C, 58.4; H, 7.5; N, 7.4%. Calculated for $C_{36}H_{54}N_4O_9S \cdot H_2O$: C, 58.7; H, 7.65; N, 7.6%.

EXAMPLE 6

To a stirred suspension of 26-(2-diethylaminoethyl)thiopristinamycin II$_B$ (isomer A)(10 g) in acetonitrile (300 cc) was added water (300 cc). Almost all of the solid dissolved and the mixture was cooled to +2° C. when ruthenium trichloride trihydrate (30 mg) was added in one portion followed one minute later by sodium metaperiodate (16.2 g) also in one portion. Stirring was continued at 0 to 2° C. for 50 minutes when the mixture was filtered and the filter pad washed with acetonitrile (50 cc). To the combined filtrate plus washings was added solid sodium bicarbonate (6 g) followed by dichloromethane (150 cc) and then sodium chloride (10.6 g), with stirring. The precipitated solid was filtered and the filter pad washed with dichloromethane (50 cc). The filtrate was mixed thoroughly and the upper organic phase separated. The lower aqueous phase was extracted with the dichloromethane washings from above. The combined organic phases were washed with saturated brine (50 cc), dried over anhydrous magnesium sulphate and filtered, the filter pad being washed with dichloromethane (50 cc). The solution so obtained, 460 cc, was treated, with stirring, with a solution of citric acid in acetone (0.2M)(68 cc), and the resulting milky solution decanted, from the brown gum (2.2 g) deposited, then filtered through diatomaceous earth to give a clear pale yellow filtrate. Evaporation under reduced pressure gave a light yellow solid (9.84 g) which was washed with ethyl acetate (100 cc) to give 26-(2-diethylaminoethyl)sulphonylpristinamycin II$_B$ (isomer A)-citrate salt as a light yellow solid (9.6 g). This material analysed for 85% 26-(2-diethylaminoethyl)sulphonylpristinamycin II$_B$ (isomer A) by analytical h.p.l.c. on reverse phase silica.

The light yellow solid (9.5 g) was dissolved in water (100 cc) and the resulting yellow solution washed with 1,1,2,2-tetrachloroethane (3×10 cc) then dichloromethane (2×10 cc). The aqueous phase was practically colourless, sodium chloride (1 g) was added and the mixture extracted six times with dichloromethane (50 cc). The combined extracts were dried over anhydrous magnesium sulphate, concentrated to 50 cc volume and light petroleum (b.p. 40°–60° C.)(100 cc) added. The resulting precipitate was filtered affording 26-(2-diethylaminoethyl)sulphonylpristinamycin II$_B$ (isomer A) hemicitrate as a white powder (3.5 g).

This material analysed for 97.3% 26-(2-diethylaminoethyl)sulphonylpristinamycin II$_B$ (isomer A) by reverse phase h.p.l.c.

By proceeding in a similar manner to that hereinbefore described to obtain 26-(2-diethylaminoethyl)sulphonylpristinamycin II$_B$ (isomer A)-citrate salt (8.0 g) as a light yellow solid which was dissolved in water (160 cc). The yellow solution was washed with dichloromethane (3×40 cc), sodium citrate (10.6 g) was added to the aqueous phase which was then extracted with dichloromethane (6×70 cc). The combined dichloromethane extracts were washed with a saturated aqueous solution of brine, dried over anhydrous magnesium sulphate and concentrated to dryness affording 26-(2-diethylaminoethyl)sulphonylpristinamycin II$_B$ (isomer A) as a pale yellow solid (3.27 g). Found: C, 59.2; H, 7.3; N, 82; S, 4.6%. Calculated for $C_{34}H_{50}N_4O_9S$: C, 59.1; H, 7.29; N, 8.11; S, 4.64%.

EXAMPLE 7

A solution of 26-(2-diethylaminoethyl)thiopristinamycin II$_B$ (isomer A)(5.0 g) in acetone (150 cc) and water (150 cc) was cooled to 0° C. (internal temperature) with vigorous stirring. Solid ruthenium trichloride trihydrate (25 mg) was added, followed immediately by addition of solid sodium metaperiodate (8.1 g). After stirring at 0° C. for 1 hour solid sodium hydrogen carbonate (5.0 g) was added to the mixture. After a further 1 minute the mixture was filtered through diatomaceous earth and the filter pad was washed with dichloromethane (200 cc). The filtrate was thoroughly mixed and the layers separated. The aqueous layer was re-extracted with fresh dichloromethane (100, then 50 cc), and the combined extracts were dried over anhydrous magnesium sulphate and evaporated to give 26-(2-diethylaminoethyl)sulphonylpristinamycin II$_B$ (isomer A) as a sandy powder (4.1 g).

EXAMPLE 8

A solution of 26-(2-diethylaminoethyl)thiopristinamycin II$_B$ (isomer A)(5.0 g) in acetone (150 cc) and water (150 cc) was cooled to 0° C. (internal temperature) with vigorous stirring. A solution of tris(triphenylphosphine)-ruthenium (II) chloride (100 mg) in acetonitrile (10 cc) was added, followed immediately by the addition of solid sodium metaperiodate (8.1 g). After stirring at 0° C. for 1 hour solid sodium hydrogen carbonate (5.0 g) was added. After stirring for a further 1 minute the mixture was filtered through diatomaceous earth, the filter pad being washed with dichloromethane (200 cc). The filtrate was mixed thoroughly, the layers allowed to separate and the aqueous layer was re-extracted with fresh dichloromethane (100 cc, then 50 cc). The combined extracts were dried over anhydrous magnesium sulphate and evaporated to give 26-(2-diethylaminoethyl)sulphonyl-pristinamycin $II_B$ (isomer A) as a light brown powder (3.9 g).

EXAMPLE 9

To a solution of 26-(2-diethylaminoethyl)sulphinyl-pristinamycin $II_B$ (isomer $A_1+A_2$)(1 g) in dichloromethane (40 cc) was added water (20 cc). The mixture was stirred rapidly, cooled to 0° C. and a solution of ruthenium trichloride trihydrate (2 mg) in water (1 cc) added, followed by a solution of sodium metaperiodate (0.634 g) in water (6 cc) in the absence of light. After 25 minutes ruthenium trichloride trihydrate (1 mg) and sodium metaperiodate (0.168 g) were added and stirring continued for a further 10 minutes. The pH of the reaction mixture was adjusted to 7 by addition of saturated aqueous sodium bicarbonate solution and extracted with dichloromethane (2×10 cc). The combined extracts were washed with water (10 cc) then extracted into dilute hydrochloric acid (0.01N)(10 ml) plus water (20 ml). The organic layer, which separated slowly, was further extracted with dilute hydrochloric acid (0.1N)(1 cc) plus water (20 cc). The combined acid extracts were treated with ethyl acetate (40 cc) followed by addition of saturated aqueous sodium bicarbonate solution to adjust the pH to 7. The organic layer was separated and the aqueous phase extracted further with ethyl acetate (30 cc). The combined organic extracts were dried over anhydrous magnesium sulphate and evaporated under reduced pressure, the residue being dried under vacuum affording 26-(2-diethylaminoethyl)sulphonylpristinamycin $II_B$ (isomer A) as a pale yellow solid (0.525 g).

EXAMPLE 10

To a solution of 26-(2-diethylaminoethyl)sulphinyl-pristinamycin $II_B$ (isomer $A_1+A_2$)(1 g) in dichloromethane (40 cc) was added water (20 cc) followed by a solution of ruthenium trichloride trihydrate (2 mg) in water (1 cc). The mixture was stirred and cooled to 0° C. when a solution of sodium metaperiodate (0.317 g) in water (3 cc) was added dropwise. After 4 minutes a further portion of sodium metaperiodate (0.317 g) in water (3 cc) was added dropwise, followed 11 minutes later by addition of ruthenium trichloride trihydrate (0.5 mg) in one portion. Six minutes later stirring was stopped, the reaction mixture decanted and a saturated aqueous solution of sodium thiosulphate added until all the excess sodium metaperiodate had been destroyed. The organic phase was separated and the aqueous phase extracted with dichloromethane (10 cc, then a further 10 cc after saturating the aqueous phase with sodium bicarbonate and sodium chloride). The combined organic phases were washed with an aqueous solution of sodium bicarbonate (10 cc, pH 7), dried over anhydrous magnesium sulphate and filtered. To the stirred filtrate was added diatomaceous earth (0.2 g) followed by dropwise addition of a solution of citric acid (0.311 g) in acetone (2 cc). The resulting mixture was filtered and the filter pad washed with a little dichloromethane. To the filtrate was added water (50 cc) followed by dilute hydrochloric acid (0.1N) to give an aqueous phase of pH 2-3 which was separated. The organic phase was further extracted with water (10 cc) plus dilute hydrochloric acid (0.1N)(1 cc). The combined acid extracts were washed with dichloromethane (10 cc), treated with carbon black and filtered through diatomaceous earth. The filtrate was treated with dichloromethane (20 cc) and a saturated aqueous solution of sodium bicarbonate to give an aqueous phase of pH 7. The organic phase was separated and the aqueous phase further extracted with dichloromethane (2×20 cc). The combined organic extracts were dried over anhydrous magnesium sulphate, concentrated to dryness and the residue dried under vacuum yielding 26-(2-diethylaminoethyl)sulphonylpristinamycin $II_B$ (isomer A) as a pale yellow solid (0.24 g).

EXAMPLE 11

A solution of 26-(2-diethylaminoethyl)sulphinylpristinamycin $II_B$ (isomer $A_1+A_2$)(882 g) in dichloromethane (15 l) was added to water (44 l). The mixture was stirred and cooled to 1°-2° C. when ruthenium trichloride trihydrate (0.88 g) in water (0.88 l) was added followed by a solution of sodium metaperiodate (447 g) in water (4.4 l) which was added dropwise. Ruthenium trichloride trihydrate (0.88 g) in water (0.88 l) was again added when half of the sodium metaperiodate solution had been added.

By proceeding in a similar manner to that hereinbefore described for the separation of the final product but by forming the acetate salt there was prepared 26-(2-diethylaminoethyl)sulphonylpristinamycin $II_B$ (isomer A)(510 g).

NMR data confirmed this is identical to the compound of Example 24 of European Patent Publication No. 191662.

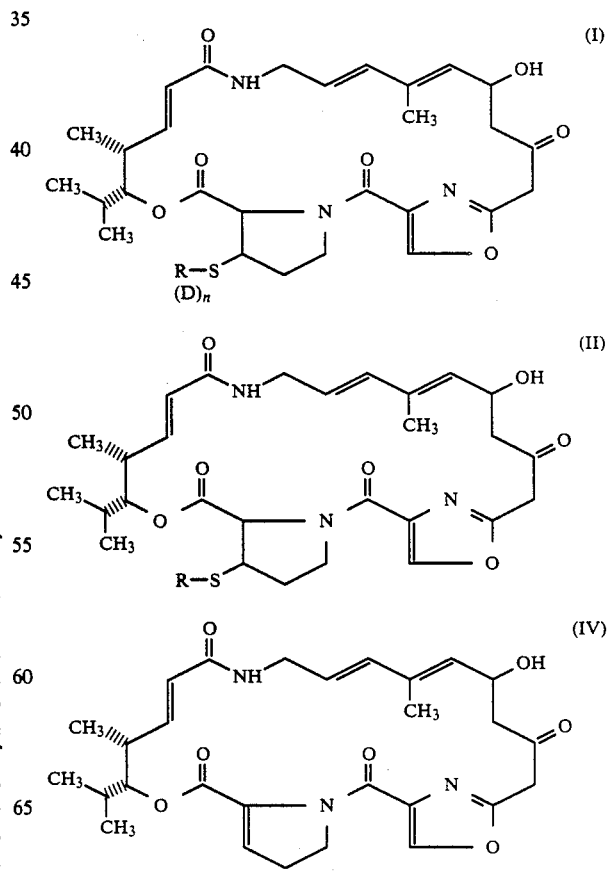

-continued

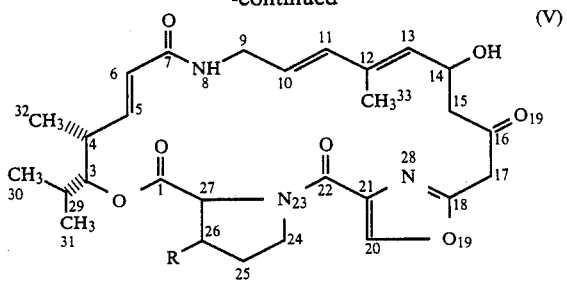

(V)

We claim:
1. Process for the preparation of a pristinamycin II$_B$ of formula

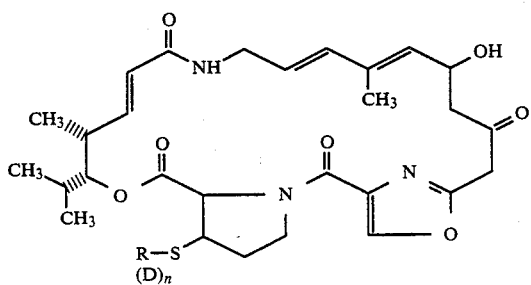

(I)

in which R denotes: either a 3-azetidinyl, 3-pyrrolidinyl, 3- or 4-piperidyl, or 3- or 4-azepinyl, each of which is unsubstituted or substituted by alkyl; or alkyl of 2 to 4 carbon atoms substituted by 1 or 2 radicals chosen from phenyl, cycloalkylamino of 3 to 6 ring atoms, N-alkyl-N-cycloalkylamino of 3 to 6 ring atoms, alkylamino, dialkylamino and dialkylcarbamoyloxy, the alkyl parts of these 2 latter radicals being unjoined or joined to form, with the nitrogen atom to which they are attached, a 1-azetidinyl, 1-pyrrolidinyl, piperidino, 1-azepinyl, morpholino, thiomorpholino in the form of sulphoxide or sulphone, 1-piperazinyl, 4-alkyl-1-piperazinyl, N-alkyl-1-homopiperazinyl, or 1-imidazolyl, all of which may be unsubstituted or substituted by alkyl, or R denotes an alkyl of 2 to 4 carbon atoms substituted by 2- or 3-azetidinyl, 2- or 3-pyrrolidinyl, 2-, 3- or 4-piperidyl, 2-, 3- or 4-azepinyl, piperazinyl, 4-alkyl-1-piperazinyl, quinolyl, isoquinolyl, or imidazolyl radical, each of which is unsubstituted or substituted by alkyl, these heterocyclic rings being linked to the substituent alkyl by a carbon atom of the said ring, at least one of the substituents carried by the said alkyl chain being a nitrogen-containing substituent capable of forming acid addition salts, or [(S)-1-methyl-2-pyrrolidinyl]-methyl, and n is 2, the aforesaid alkyl radicals and moieties being linear or branched and containing, unless otherwise stated, 1 to 10 carbon atoms, and its isomers and their mixtures, and its acid addition salts, which comprises oxidizing a compound of formula I as hereinbefore defined in which n is 1 or a compound of formula I as hereinbefore defined in which n is 0, with a periodic acid salt and a catalytic amount of ruthenium (VIII).

2. Process according to claim 1 in which the catalytic amount of ruthenium (VIII) is prepared in situ by oxidation of a ruthenium compound of a lower oxidation state.

3. Process according to claim 1 in which the ruthenium (VIII) is prepared in situ by oxidation of ruthenium dioxide dihydrate, ruthenium trichloride trihydrate or tris(triphenylphosphine)ruthenium (II) chloride.

4. Process according to claim 1 in which a compound of formula (II) is oxidized with a periodic acid salt and a catalytic amount of ruthenium trichloride trihydrate in acetonitrile and water.

5. Process according to claim 1 in which a compound of formula I in which n is 1 is oxidized with a periodic acid salt and a catalytic amount of ruthenium trichloride trihydrate in dichloromethane and water.

6. Process according to claim 1 in which the oxidation is effected in an aqueous medium at a temperature from −5° C. to ambient temperature.

7. Process according to claim 1 in which the starting material is a compound of formula I in which n is 1 and the molar ratio of the periodate to the said starting material is 1:6:1 to 5:1.

8. Process according to claim 1 in which the starting material is a compound of formula II and the molar ratio of the said periodate to the said starting material is 5:1 to 7:1.

* * * * *